United States Patent
Lee et al.

(10) Patent No.: US 12,209,916 B2
(45) Date of Patent: Jan. 28, 2025

(54) COMPOSITION FOR TEMPERATURE SENSORS INCLUDING GRAPHENE OXIDE, DNAZYME AND PNA AND TEMPERATURE SENSING METHOD USING THE SAME

(71) Applicant: Korea Research Institute of Chemical Technology, Daejeon (KR)

(72) Inventors: Jieon Lee, Daejeon (KR); Woo-keun Kim, Daejeon (KR); Seokjoo Yoon, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 217 days.

(21) Appl. No.: 17/023,003

(22) Filed: Sep. 16, 2020

(65) Prior Publication Data

US 2021/0080333 A1 Mar. 18, 2021

(30) Foreign Application Priority Data

Sep. 16, 2019 (KR) ........................ 10-2019-0113372

(51) Int. Cl.
| | |
|---|---|
| *C12Q 1/6816* | (2018.01) |
| *C01B 32/198* | (2017.01) |
| *G01K 11/12* | (2021.01) |
| *G01N 27/414* | (2006.01) |

(52) U.S. Cl.
CPC ............ *G01K 11/12* (2013.01); *C01B 32/198* (2017.08); *C12Q 1/6816* (2013.01); *G01N 27/4145* (2013.01); *G01N 27/4146* (2013.01)

(58) Field of Classification Search
CPC .................................................. C01B 32/198
See application file for complete search history.

(56) References Cited

PUBLICATIONS

Lee et al., A biosensor for the detection of single base mismatches in microRNA, Chem. Commun., 2015, 51, pp. 14597-14600 (Year: 2015).*
Gong et al., DNAzyme-based biosensors and nanodevices, Chem. Commun., 2015, 51: 979-995 (Year: 2015).*
Chen et al., One-step reduction and PEGylation of graphene oxide for photothermally controlled drug delivery, Biomaterials, 2014, 35: 4986-4995 (Year: 2014).*
Bu et al., DNA nanostructure-based fluorescence thermometer with silver nanoclusters, Nanotechnology, 2018, 16 pages.
Donner et al., Mapping Intracellular Temperature Using Green Fluorescent Protein, 2012, Nano Letters, pp. 2017-2111, vol. 12, American Chemical Society.
Hu et al., Intracellular Cascade FRET for Temperature Imaging of Living Cells with Polymeric Ratiometric Fluorescent Thermometers, 2015, ACS Applied Materials & Interfaces, 32 pages, American Chemical Society.
Yamamoto et al., Efficient Skin Temperature Sensor and Stable Gel-Less Sticky ECG Sensor for a Wearable Flexible Healthcare Patch, 2017, Advanced Healthcare Materials, 7 pages.
Boles et al., Quantification of Mitochondrial DNA Heteroplasmy by Temporal Temperature Gradient Gel Electrophoresis, 2003, Clinical Chemistry, pp. 198-200, vol. 49, No. 1.
Freddi et al., A Molecular Thermometer for Nanoparticles for Optical Hyperthermia, 2013, Nano Letters, 7 pages, American Chemical Society.
Jonstrup et al., DNA Hairpins as Temperature Switches, Thermometers and Ionic Detectors, 2013, Sensors, pp. 5938-5944, vol. 13.

* cited by examiner

*Primary Examiner* — Ekaterina Poliakova-Georgantas
(74) *Attorney, Agent, or Firm* — Klarquist Sparkman, LLP

(57) ABSTRACT

The present invention relates to a composition for temperature sensors including graphene oxide, DNAzyme and PNA, a temperature sensing method and a kit using the same. In the present invention, when the DNAzyme/PNA duplex is dissociated at a certain temperature, graphene oxide adsorbs PNA with excellent selectivity and irreversibility, enabling recall of temperature, to permit delayed color development in the time of need. Also, the target temperature can be easily and quickly detected with the naked eye through the color change of the colorimetric reagent, and the thermosensor is technically convenient and easy to apply, so it can be used in various biological applications. Moreover, it can be used as a barcode (on/off) system using a combination of PNA probes with various lengths, and thus can be broadly applied to sensing a diverse range of temperatures.

16 Claims, 16 Drawing Sheets
Specification includes a Sequence Listing.

FIG. 2A

```
Dz  5' - GGG TAG GGC GGG TTG GGA -3'
         ... ... ...
P18 3' - CCC ATC CCC CGG AAC CCT -FAM -5'
```

FIG. 2B

■ Comparative Example 2
□ Example 1
▨ None

| Name | Sequence |
|------|----------|
| Dz | 5' – GGG TAG GGC GGG TTG GGA     –3' |
| P9 | 3' –         TC CCG CCC A       – FAM –5' |
| P12 | 3' –       ATC CCG CCC AAC     – FAM –5' |
| P18 | 3' – CCC ATC CCG CCC AAC CCT – FAM –5' |

COMPOSITION FOR TEMPERATURE SENSORS INCLUDING GRAPHENE OXIDE, DNAZYME AND PNA AND TEMPERATURE SENSING METHOD USING THE SAME

INCORPORATION OF ELECTRONIC SEQUENCE LISTING

The Sequence Listing is submitted as an ASCII text file named "Sequence.txt" created on Oct. 13, 2023 (2,201 bytes), which is incorporated by reference herein.

BACKGROUND OF THE INVENTION

1. Field of the Invention

The present invention relates to a composition for temperature sensors including graphene oxide, DNAzyme and PNA and a temperature sensing method using the same

2. Description of the Related Art

Temperature is a fundamental parameter in most branches of sciences and technology. Conventionally, many temperature sensors have been established based on temperature-responsive materials, such as biomolecules (non-patent reference 1, Bu et al., 2018. DNA nanostructure-based fluorescence thermometer with silver nanoclusters. Nanotechnology 29(29), 295501; non-patent reference 2, Donner et al., 2012. Mapping intracellular temperature using green fluorescent protein. Nano Lett 12(4), 2107-2111), polymers (non-patent reference 3, Hu et al., 2015. Intracellular cascade FRET for temperature imaging of living cells with polymeric ratiometric fluorescent thermometers. ACS Appl Mater Interfaces 7(2018), 15551-15560), hydrogels (non-patent reference 4, Yamamoto et al., 2017. Efficient Skin Temperature Sensor and Stable Gel-Less Sticky ECG Sensor for a Wearable Flexible Healthcare Patch. Adv Healthc Mater 6(17)), organic small molecules (non-patent reference 5, Boles at al., 2003. Quantification of mitochondrial DNA heteroplasmy by temporal temperature gradient gel electrophoresis. Clin Chem 49(1), 198-200), and nanomaterials (non-patent reference 6, Freddi et al., 2013. A molecular thermometer for nanoparticles for optical hyperthermia. Nano Lett 13(5), 2004-2010).

Among these materials, DNA-based nanostructures are one of the most valuable tools for sensing temperature owing to their programmability, high temperature resolution, and fast response. Hydrogen bonds between the bases of a DNA duplex are broken at elevated temperatures, a process called "DNA melting". Because the melting kinetics of DNA is correlated to the increase in temperature, the fraction of melted DNA acts as a temperature indicator. The detectable temperature range of such a thermosensor is determined by the melting temperature (Tm) of the DNA structure. For example, the molecular beacon (MB), designed to form a stem-loop structure, is a representative DNA nanothermosensor that acts via temperature-responsive hairpin opening (non-patent reference 7, Jonstrup et al., 2013. DNA hairpins as temperature switches, thermometers and ionic detectors. Sensors (Basel) 13(5), 5937-5944).

Most DNA thermosensors are based on fluorescence methods and exploit the fluorescence resonance energy transfer phenomenon between fluorescent dyes bound to the DNA structure. Indeed, few naked-eye colorimetric approaches for temperature measurement have been developed, despite their technical simplicity and applicability in practical fields, such as health diagnostics and food safety. Guanine (G)-rich DNAzyme (Dz) is one of the most useful DNAs for various bio-applications. Guanine (G)-rich DNAzyme (Dz) adopts a G-quadruplex structure and exhibits peroxidase-like activity in the presence of hemin. This catalytic DNA molecule has been widely utilized in numerous colorimetric sensing systems in place of peroxidases owing to its thermal stability, ease of functionalization, and cost-effectiveness Thus, the present inventors have developed a temperature sensor that can be read with the naked eye using peptide nucleic acid (PNA), DNAzyme (Dz) and PEGylated graphene oxide (PEG-GO), which can be easily applied in practical fields such as health diagnostics and food safety.

SUMMARY OF THE INVENTION

It is an object of the present invention to provide a composition for temperature sensors including graphene oxide, a duplex in which a DNAzyme strand and a PNA strand are complementarily linked and a DNAzyme cofactor, and enabling naked-eye colorimetric measurement and temperature recall.

It is another object of the present invention to provide a method for temperature sensing using the composition for temperature sensors enabling naked-eye colorimetric measurement.

It is another object of the present invention to provide a kit for temperature sensors comprising the composition for temperature sensors enabling naked-eye colorimetric measurement.

To achieve the above objects, in an aspect of the present invention, the present invention provides a composition for temperature sensors including graphene oxide, a duplex in which a DNAzyme strand and a PNA strand are complementarily linked and a DNAzyme cofactor.

In another aspect of the present invention, the present invention provides a method for temperature sensing comprising the following steps:

obtaining a mixture containing a duplex in which the DNAzyme strand and the PNA strand are complementarily linked by mixing the DNAzyme strand and the PNA strand;

adding graphene oxide to the mixture; and observing the color change of the mixture while heating the mixture.

In another aspect of the present invention, the present invention provides a kit for temperature sensors comprising the composition for temperature sensors including graphene oxide, a duplex in which a DNAzyme strand and a PNA strand are complementarily linked and a DNAzyme cofactor.

Advantageous Effect

In the composition for temperature sensors, the method for temperature sensing, and the kit for temperature sensors according to the present invention, when the DNAzyme/PNA duplex is dissociated at a certain temperature, graphene oxide adsorbs PNA with excellent selectivity and irreversibility, so it is enabled recall of temperature, which can permit delayed color development in the time of need. In addition, the target temperature can be easily and quickly detected with the naked eye through the color change of the colorimetric reagent, and the thermosensor is technically convenient and easy to apply, so it can be used in various biological applications. Moreover, it can be used as a barcode (on/off) system using a combination of PNA probes with various lengths, and thus can be broadly applied to sensing a diverse range of temperatures.

BRIEF DESCRIPTION OF THE DRAWINGS

FIG. 2A is a diagram showing the sequences of Dz strand (SEQ ID NO: 1) and its complementary PNA strand (SEQ ID NO: 4).

FIG. 2B is a diagram showing the results of observing the color changes in the presence of a Dz cofactor of Comparative Example 2, a color reagent of Example 1, and the negative control peroxide.

DETAILED DESCRIPTION OF THE INVENTION

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

As described above, in the past, many temperature sensors using biomolecules, organic small molecules, nanomaterials, etc. have been established, but few naked-eye colorimetric approaches for temperature measurement have been developed, and there are limitations in practical applications such as health diagnostics and food safety.

Thus, in order to solve the above problems, the present inventors have developed a temperature sensor that can be identified with the naked eye and can be easily applied in practical fields such as health diagnostics and food safety using peptide nucleic acid (PNA), DNAzyme (Dz) and graphene oxide.

The present inventors established a G-rich Dz-based colorimetric temperature sensor using peptide nucleic acid (PNA) and PEGylated graphene oxide (PEG-GO). Graphene oxide (GO), a water-dispersive form of graphene, is a two-dimensional carbon sheet harboring various oxygen-containing groups. These surface groups can easily be functionalized with polyethylene glycol (PEG), which confers high biocompatibility and dispersibility to GO. GO has been utilized for various bio-applications, such as in biosensors and drug delivery systems for several decades. In numerous biosensors, GO has generally shown preferential affinity for single-stranded nucleic acids compared with the duplex form and exhibits efficient fluorescence-quenching capability. Peptide nucleic acid (PNA), a synthetic DNA mimic, is currently of great interest for use in GO-based sensors. Compared with DNA, uncharged PNA shows superior binding affinity towards GO and improved thermal stability upon binding to complementary DNA or RNA. Thus, the present inventors utilized the combination of PNA and PEG-GO to control the catalytic activity of Dz in a temperature-dependent manner, permitting colorimetric thermal visualization.

Figure 1:
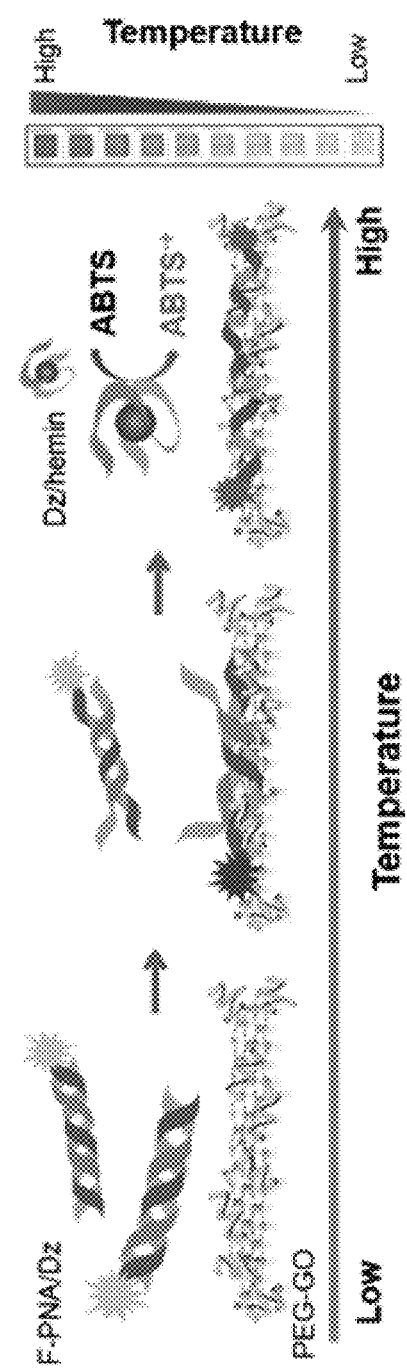
FIG. 1 is a diagram showing the schematic mechanism of a temperature sensing method using a composition for temperature sensors including PNA and PEG-GO.

The mechanism for the temperature sensor according to the present invention relied on thermosensitive Watson-Crick base paring with G-rich Dz and the G-quadruplex conformation of Dz with catalytic activity. To control the Dz activity according to temperature, the present inventors employed a C-rich PNA probe to hybridize with Dz strand and PEG-GO as a scavenger for the PNA probe. As an example of the composition for temperature sensors according to the present invention, a temperature sensor was prepared by mixing annealed Dz/PNA duplex with PEG-GO in 1×Dz buffer containing hemin and 2,2'-azino-bis(3-ethylbenzothiazoline-6-sulfonic acid) (ABTS)). At this time, the G-quadruplex folding of Dz was perfectly blocked by strong Watson-Crick base pairing with complementary PNA, resulting in inhibition of Dz activity. The duplex was denatured by increasing the temperature, followed by selective PNA capture by PEG-GO, which allowed Dz to fold into the G-quadruplex structure. The adsorption of PNA on PEG-GO occurred irreversibly; thus, the amount of active Dz could be quantitatively determined according to the ratio of denaturation of Dz/PNA at the target temperature, even after the temperature returned to lower baseline. As a result, the G-quadruplex Dz combined with the Dz cofactor and catalyzed the reaction to produce a colorimetric reagent by post-addition of peroxide (FIG. 1).

In an aspect of the present invention, the present invention provides a composition for temperature sensors including graphene oxide, a duplex in which a DNAzyme strand and a PNA strand are complementarily linked and a DNAzyme cofactor.

The term PNA (peptide nucleic acid) as used in the present invention includes the substitution of a sugar-phosphate skeleton of DNA with a peptide conjugate, and can have a neutral structure that does not exhibit negative charge of the DNA backbone structure.

The term DNAzyme (Dz) as used in the present invention generally refers to a nucleic acid molecule having enzymatic activity. For example, DNAzyme can have peroxidase activity. In addition, DNAzyme can be a term including Deoxyribozymes, DNA enzymes, DNAzymes, catalytic DNA, DNA-based enzymes, and can also be ribonuclease and RNA ligase. DNAzyme may also enable chemical reactions such as DNA phosphorylation, DNA adenylation, DNA deglycosylation, porphyrin metalation, thymine dimer photoreversion and DNA cleavage.

DNAzyme may include a DNAzyme sequence, and the DNAzyme sequence refers to a sequence in which a nucleic acid construct capable of functioning as DNAzyme can be formed. For example, it can be a sequence capable of forming a nucleic acid quadruplex structure, and in one embodiment, a sequence capable of forming a G-quadruplex.

Further, the length of the duplex in which the DNAzyme strand and the PNA strand are complementarily linked can be, for example, 5 to 50 nucleotides, 5 to 40 nucleotides, to 30 nucleotides, 5 to 25 nucleotides, 6 to 20 nucleotides, and 9 to 18 nucleotides, but not always limited thereto. At least a part of the DNAzyme strand can be complementary to at least a part of the PNA strand.

Figures 7A, 7B:
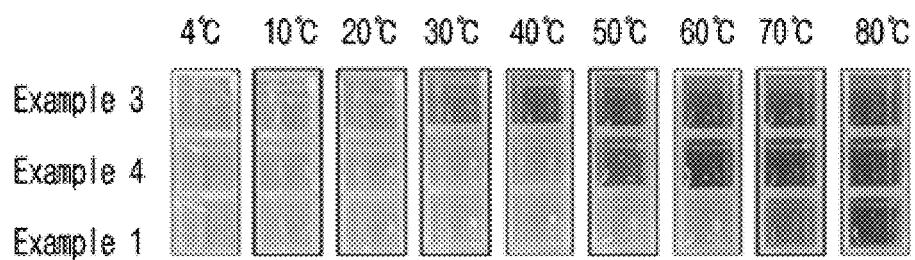
FIG. 7A, FIG. 7B, FIG. 7C, FIG. 7D, and FIG. 7E are a set of diagrams showing the results of measuring the fluorescence intensity and absorbance of the products of Example 1, Example 3 and Example 4 for colorimetric confirmation of the temperature sensor according to the number of base pairs. The sequences shown in FIG. 7A include Dz (SEQ ID NO: 1), P9 (SEQ ID NO: 2), P12 (SEQ ID NO: 3) and P18 (SEQ ID NO: 4).
Figure 7C:
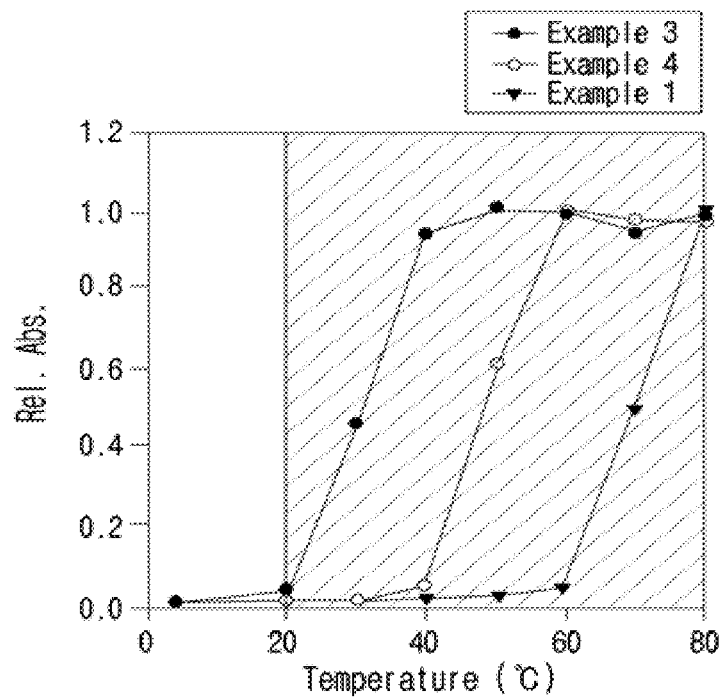

In an embodiment of the present invention, as shown in FIG. 7A, the DNAzyme sequence can be 5'-GGG TAG GGC GGG TTG GGA-3' (SEQ. ID. NO: 1). In addition to this, if it can form a G-quadruplex, it is included in the present invention without limitation.

In one embodiment, a DNAzyme sequence comprising 5'-GTGGGGCATTGTGGGTGGGTGTGG-3'(SEQ. ID. NO: 5), 5'-GTGGGTAGGGCGGGTTGG-3'(SEQ. ID. NO: 6), 5'-GGTGGTGGTGGTTGTGGTGGTGGTGG-3'(SEQ. ID. NO: 7), or 5'-GGGTTAGGGTTAGGGTTAGGG-3' (SEQ. ID. NO: 8) can be used instead of 5'-GGG TAG GGC GGG TTG GGA-3'(SEQ. ID. NO: 1).

In another aspect of the present invention, the duplex can be denatured into a single strand at a certain temperature, so that the DNAzyme strand can bind to the DNAzyme cofactor.

In one aspect of the present invention, the DNAzyme cofactor can be understood to be included in the present invention without limitation as long as it can be used to function as DNAzyme together with the sequence of the DNAzyme. In an embodiment of the present invention, the DNAzyme can be one that exhibits peroxidase activity, and the DNAzyme cofactor can be hemin.

At this time, the duplex is irreversibly denatured into a single strand at a certain temperature, and the DNAzyme strand can bind to the DNAzyme cofactor. The target temperature can be memorized even if the time passes or the temperature changes, so that the target temperature may be sensed by adding a colorimetric reagent.

In another aspect of the present invention, the graphene oxide can be polyethylene glycol (PEG)-functionalized graphene oxide (PEG-GO). The step of preparing PEG-GO by functionalizing graphene oxide with polyethylene glycol can include carboxylation. In addition, the step of preparing PEG-GO by functionalizing graphene oxide with polyethylene glycol can include PEGylation (polyethylene glycolation).

In an aspect of the present invention, the graphene oxide can be in the form of a single layer sheet form, but not always limited thereto. For example, the graphene oxide, which is in the form of a single layer sheet, has a large surface area at the same mass compared to the graphene oxide, which is not in the form of a single layer sheet, so that a large amount of nucleic acid probes can be adsorbed.

In an aspect of the present invention, the graphene oxide can be in the form of particles having a size of about 10 nm to about 1 μm, but not always limited thereto. For example, the size of the graphene oxide particles can be about 10 nm to about 1 μm, about 10 nm to about 700 nm, about 10 nm to about 500 nm, about 10 nm to about 400 nm, about 10 nm to about 300 nm, about 10 nm to about 200 nm, about 10 nm to about 100 nm, about 10 nm to about 50 nm, about 50 nm to about 1 μm, about 100 nm to about 1 μm, about 200 nm to about 1 μm, about 300 nm to about 1 μm, about 400 nm to about 1 μm, about 500 nm to about 1 μm, about 700 nm to about 1 μm, about 200 nm to about 300 nm, or about 400 nm or less, but not always limited thereto.

In another aspect of the present invention, the composition can further include a colorimetric reagent, and the colorimetric reagent can be included in the composition of the present invention without limitation as long as it is capable of exhibiting colorimetry by DNAzyme activity. For example the colorimetric reagent can be ABTS (2,2'-azino-bis(3-ethylbenzothiazoline-6-sulfonic acid)), OPD (o-phenylenediamine dihydrochloride), DAB (diaminobenzidine), AEC (3-amino-9-ethylcarbazole), TMB (3,3',5,5'-tetra methylbenzidine), AmplexRed, or Homovanilic acid. In addition, the colorimetric reagent can include one or more peroxides.

In a preferred embodiment of the present invention, the present invention is not limited to a specific theory, but the DNAzyme exhibits peroxidase activity. The DNAzyme can detect colorimetry from one or more selected from the group consisting of the ABTS, OPD, DAB, AEC, TMB, AmplexRed, and Homovanilic acid through a series of oxidation-reduction processes of the at least one peroxide with one or more selected from the group consisting of the ABTS, OPD, DAB, AEC, TMB, AmplexRed, and Homovanilic acid.

In another aspect of the present, the composition for temperature sensors can control the target temperature by adjusting the length of the PNA strand.

In another aspect of the present invention, the present invention provides a method for temperature sensing comprising the following steps:
  obtaining a mixture containing a duplex in which the DNAzyme strand and the PNA strand are complementarily linked by mixing the DNAzyme strand and the PNA strand;
  adding graphene oxide to the mixture; and
  observing the color change of the mixture while heating the mixture.

Hereinafter, the method for temperature sensing is described in detail step by step.

The step of obtaining a mixture containing a duplex in which the DNAzyme strand and the PNA strand are complementarily linked by mixing the DNAzyme strand and the PNA strand can be accomplished by annealing the DNAzyme strand and the PNA strand and slowly cooling. In the examples described below, the duplex was prepared by annealing the DNAzyme strand and the PNA strand at 95° C. for 5 minutes and slowly cooling in water, but the conditions may vary depending on the length of the DNAzyme strand and the PNA strand and the type of nucleotide.

The step of adding graphene oxide to the mixture can be understood as adding graphene oxide (GO) to the obtained mixture. The graphene oxide can be polyethylene glycol (PEG)-functionalized graphene oxide (PEG-GO). The step of preparing PEG-GO by functionalizing graphene oxide with polyethylene glycol can include carboxylation. In addition, the step of preparing PEG-GO by functionalizing graphene oxide with polyethylene glycol can include PEGylation (polyethylene glycolation).

The step of observing the color change of the mixture while heating the mixture can include a process of observing the moment when the color of the mixture changes while heating the mixture, or heating the mixture until the color changes. The step can further include a step of adding a DNAzyme cofactor to the mixture. At this time, the duplex can be denatured into a single strand at a certain temperature, so that the DNAzyme strand can bind to the DNAzyme cofactor. The DNAzyme cofactor can be understood to be included in the present invention without limitation as long as it can be used to function as DNAzyme together with the sequence of the DNAzyme. In an embodiment of the present invention, the DNAzyme can be one that exhibits peroxidase activity, and the DNAzyme cofactor can be hemin.

The composition can further include a colorimetric reagent, and the colorimetric reagent can be included in the composition of the present invention without limitation as long as it is capable of exhibiting colorimetry by DNAzyme activity. For example the colorimetric reagent can be ABTS (2,2'-azino-bis(3-ethylbenzothiazoline-6-sulfonic acid)), OPD (o-phenylenediamine dihydrochloride), DAB (diaminobenzidine), AEC (3-amino-9-ethylcarbazole), TMB (3,3',5,5'-tetra Methylbenzidine), AmplexRed, or Homovanilic acid. In addition, the colorimetric reagent can include one or more peroxides.

The method for temperature sensing can control the target temperature by adjusting the length of the PNA strand. Adjusting the length of the PNA strand may mean controlling the temperature at which the duplex is denatured by controlling the number of hydrogen bonds between the PNA strand and the DNAzyme strand. This may include controlling the temperature at which the duplex is denatured by controlling the number of binding of adenine (A) and thymine (T) or the number of binding of guanine (G) and cytosine (C). In the examples described below, experiments were performed on target temperature control through the control of the PNA strand length using 9 mer PNA(P9) 3'-TC CCG CCC A-5' (SEQ. ID. NO: 2), 12 mer PNA(P12) 3'-ATC CCG CCC AAC-5' (SEQ. ID. NO: 3), 18 mer PNA(P18) 3'-CCC ATC CCG CCC AAC CCT-5' (SEQ. ID. NO: 4), 11 mer PNA(P11) 3'-ATC CCG CCC AA-5' (SEQ. ID. NO: 9) and 10 mer PNA(P10) 3'-ATC CCG CCC A-5' (SEQ. ID. NO: 10). In Experimental Example 6 described below, it was confirmed that as the length of the PNA strand was increased, the temperature at which color began to increase was increased.

In another aspect of the present invention, the present invention provides a kit for temperature sensors comprising the composition including graphene oxide, a duplex in which a DNAzyme strand and a PNA strand are complementarily linked and a DNAzyme cofactor.

The kit can further include a colorimetric reagent, and the colorimetric reagent can be included in the kit of the present invention without limitation as long as it is capable of exhibiting colorimetry by DNAzyme activity. For example the colorimetric reagent can be ABTS (2,2'-azino-bis(3-ethylbenzothiazoline-6-sulfonic acid)), OPD (o-phenylenediamine dihydrochloride), DAB (diaminobenzidine), AEC (3-amino-9-ethylcarbazole), TMB (3,3',5,5'-tetra Methylbenzidine), AmplexRed, or Homovanilic acid. In addition, the colorimetric reagent can include one or more peroxides.

The graphene oxide can be polyethylene glycol (PEG)-functionalized graphene oxide (PEG-GO). The step of preparing PEG-GO by functionalizing graphene oxide with polyethylene glycol can include carboxylation. In addition, the step of preparing PEG-GO by functionalizing graphene oxide with polyethylene glycol can include PEGylation (polyethylene glycolation).

In another aspect of the present, the kit can control the target temperature by adjusting the length of the PNA strand.

Hereinafter, the present invention will be described in detail by the following examples.

However, the following examples and experimental examples are only for illustrating the present invention, and the contents of the present invention are not limited thereto.

DNA strands were purchased from Genotech (Daejon, Korea).

PNA strands were purchased from Panagene (Daejon, Korea).

Hemin, 2,2'-azino-bis(3-ethylbenzothiazoline-6-sulfonic acid) (ABTS), chloroacetic acid, and GO were purchased from Sigma-Aldrich (MO, USA).

1-Ethyl-3-(3-dimethylaminopropyl)carbodiimide hydrochloride (EDC) was purchased from ThermoFisher Scientific (OK, USA).

Amine-functionalized methoxypolyethylene glycol (mPEG-NH2, molecular weight: 2000 Da) was purchased from NANOCS (Boston, MA, USA).

Amicon Ultra 0.5 mL Centrifugal Filters were purchased from Merck Millipore (Darmstadt, Germany).

Temperature control was performed using a thermocycler (Bio-Rad, USA).

Absorbance and fluorescence were measured using a Citation 5 multimode reader (Biotek, USA).

<Preparative Example 1> Preparation of PEG-GO by PEG Modification of GO

For carboxylation, 0.2 mg/mL GO was prepared in 4 M NaOH solution containing 2 mg/mL chloroacetic acid. The mixture was bath-sonicated for 75 minutes and purified by centrifugation at 15000 rpm for 30 minutes twice. The carboxylated GO was dialyzed against deionized (DI) water for 1 week. As a result, GO—COOH was obtained.

For PEGylation, 1.5 mL carboxylated GO (1 mg/mL) was mixed with 4 μmol mPEG-NH$_2$ (amine-functionalized methoxypolyethylene glycol, molecular weight: 2000 Da, purchased from NANOCS (Boston, MA, USA)) and bath-sonicated for 5 minutes. Subsequently, 1-ethyl-3-(3-dimethylaminopropyl)carbodiimide hydrochloride (EDC) was added to a concentration of 5 mM and the solution was bath-sonicated for another 30 minutes. To further increase the concentration, more EDC was added with shaking for 12 hours. The fabricated PEG-GO was purified with deionized water using a 50 k centrifugal filter unit at 10000 rpm for 15 minutes. The washing step was repeated five times. As a result, PEG-GO (polyethylene glycol-functionalized graphene oxide) was prepared.

Example 1

The present inventors prepared an 18 mer G-rich Dz strand and its fully complementary sequenced FAM-labeled PNA strand (P18) (FIG. 2A). The Dz/P18 duplex was prepared by annealing the Dz and P18 at 95° C. for 5 minutes and slowly cooling in water.

Example 2

500 nM of the Dz/P18 duplex of Example 1 was prepared with PEG-GO in 1×Dz buffer containing hemin and ABTS. The samples were then applied at 95° C. for 5 minutes to completely denature the Dz from PNA.

Example 3

The present inventors prepared a 9 mer G-rich Dz strand and its fully complementary sequenced FAM-labeled PNA strand (P9). The Dz/P9 duplex was prepared by annealing the Dz and P9 at 95° C. for 5 minutes and slowly cooling in water.

Example 4

The present inventors prepared a 12 mer G-rich Dz strand and its fully complementary sequenced FAM-labeled PNA strand (P12). The Dz/P12 duplex was prepared by annealing the Dz and P12 at 95° C. for 5 minutes and slowly cooling in water.

Example 5

The present inventors prepared a 10 mer G-rich Dz strand and its fully complementary sequenced FAM-labeled PNA strand (P10). The Dz/P10 duplex was prepared by annealing the Dz and P10 at 95° C. for 5 minutes and slowly cooling in water.

Example 6

The present inventors prepared a 11 mer G-rich Dz strand and its fully complementary sequenced FAM-labeled PNA strand (P11). The Dz/P11 duplex was prepared by annealing the Dz and P11 at 95° C. for 5 minutes and slowly cooling in water.

Comparative Example 1

For carboxylation of GO (purchased from Sigma-Aldrich (MO, USA)), 0.2 mg/mL GO was prepared in 4 M NaOH solution containing 2 mg/mL chloroacetic acid. The mixture was bath-sonicated for 75 minutes and purified by centrifugation at 15000 rpm for 30 minutes twice. The carboxylated GO was dialyzed against deionized (DI) water for 1 week. As a result, GO—COOH was obtained.

Comparative Example 2

An 18 mer free Dz without complementary PNA was prepared (FIG. 2A).

Comparative Example 3

500 nM of the Dz/P18 duplex of Example 1 was prepared with PEG-GO in 1×Dz buffer containing hemin and ABTS, which was then stored at room temperature without heating.

<Experimental Example 1> Confirmation of Enhanced Dispersibility of PEG-GO

Figure 3:
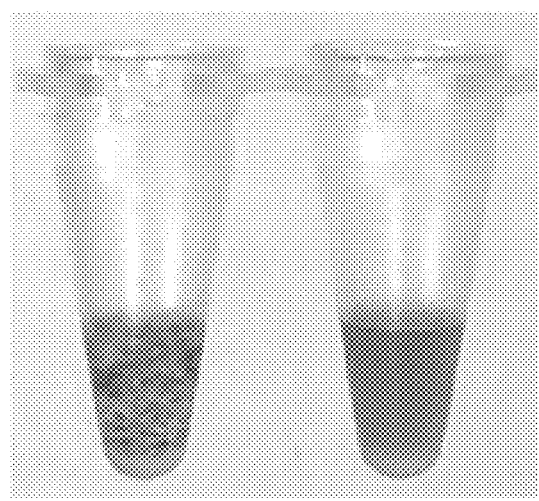
FIG. 3 is a photograph showing the dispersibility of GO—COOH of Comparative Example 1 and PEG-GO of Preparative Example in 5×PBS solution.

To confirm the dispersibility of the PEG-GO synthesized in Preparative Example 1, the PEG-GO of Preparative Example 1 and the GO—COOH of Comparative Example 1 were prepared. The results are shown in FIG. 3.

First, the PEG-GO of Preparative Example 1 and the GO-COOH of Comparative Example 1 were added to high-salt buffer (5×PBS) to confirm whether or not aggregation occurred in the solution phase. As a result, the PEG-GO of Preparative Example 1 showed an enhanced dispersibility in high-salt buffer (5×PBS), whereas the GO—COOH of Comparative Example 1 was aggregated and was observed with the naked eye in the buffer (FIG. 3). From the above results, it was confirmed that PEGylation enhanced the dispersibility of GO in a salt-rich aqueous solution.

<Experimental Example 2> Confirmation of Selectivity of PEG-GO for PNA

To confirm the selectivity of PEG-GO for PNA, the PEG-GO of Preparative Example 1, the GO—COOH of Comparative Example 1, FAM-labeled 18 mer PNA strand (P18) and DNA strand with the same sequence as P18 (D18) were prepared. The results are shown in FIG. 4A to FIG. 4F.

Figure 4A:
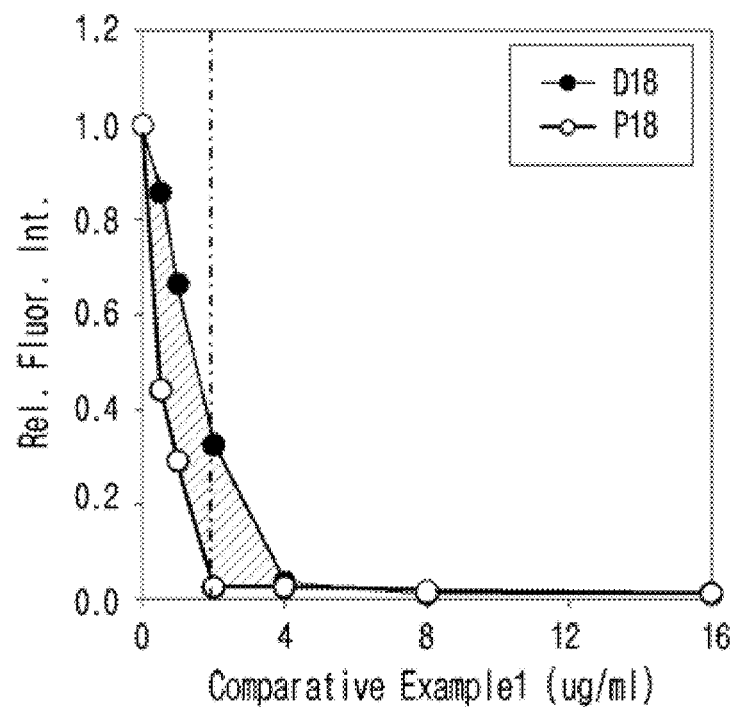
FIG. 4A, FIG. 4B, FIG. 4C, FIG. 4D, FIG. 4E, and FIG. 4F are set of graphs showing the results of observing the quenching phenomenon when the DNA strand (D18) and PNA strand (P18) were mixed with GO—COOH of Comparative Example 1 and PEG-GO of Preparative Example.
Figure 4B:
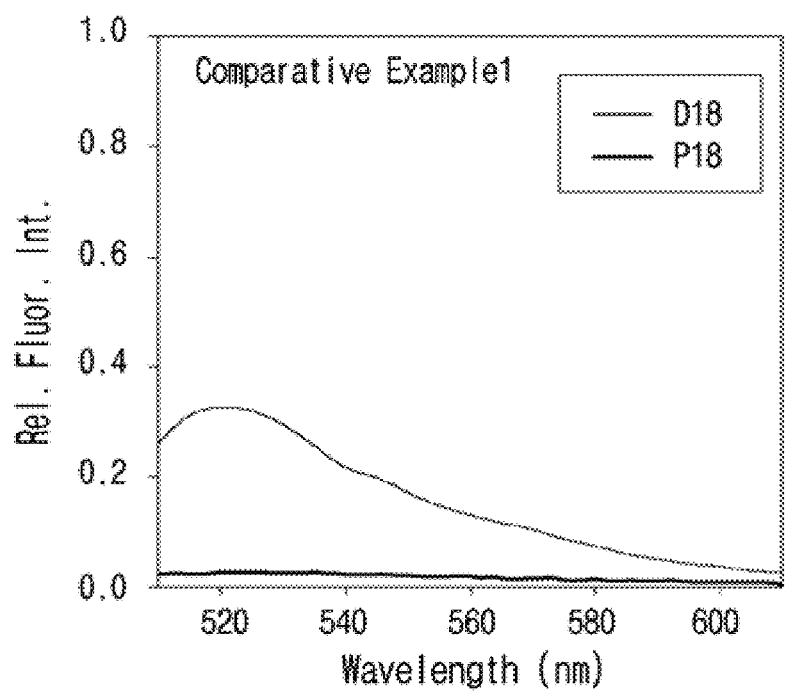
Figure 4C:
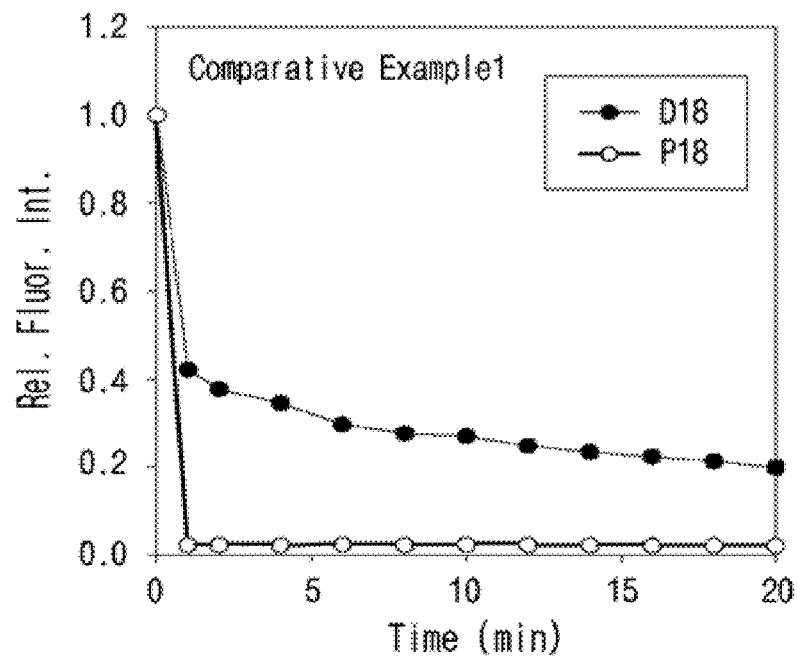
Figure 4D:
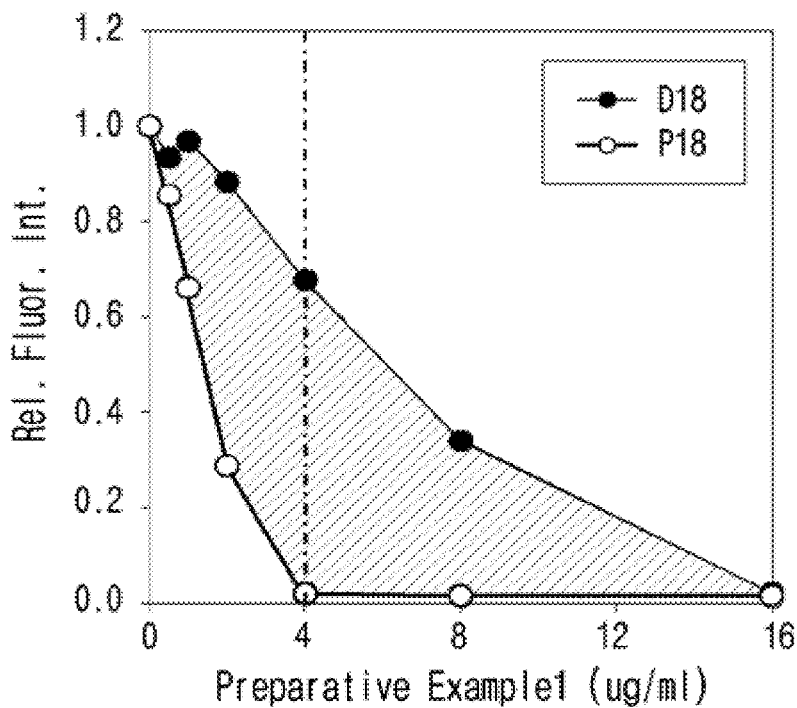

Each 100 nM of P18 and D18 were prepared in 1×Dz buffer and mixed with various concentrations (0~16 μg/ml) of the PEG-GO of Preparative Example 1 and the GO—COOH of Comparative Example 1. As a result, P18 showed higher quenching efficiency than D18 in the presence of the GO-COOH of Comparative Example 1 (FIG. 4A). The PEG-GO of Preparative Example 1 increased the difference in quenching efficiency between D18 and P18 compared with that of the GO—COOH of Comparative Example 1 (FIG. 4D). Only 2-fold more the GO—COOH of Comparative Example 1 was required to quench the intensity of D18 compared with P18, whereas 4-fold more the PEG-GO of Preparative Example 1 was required for D18 than for P18. From the above results, it was confirmed that the PEG-GO of Preparative Example 1 had superior selectivity to PNA compared to the GO—COOH of Comparative Example 1. It was also confirmed that the optimal amount of PEG-GO for complete adsorption of PNA was 4 μg/mL.

Figure 4E:
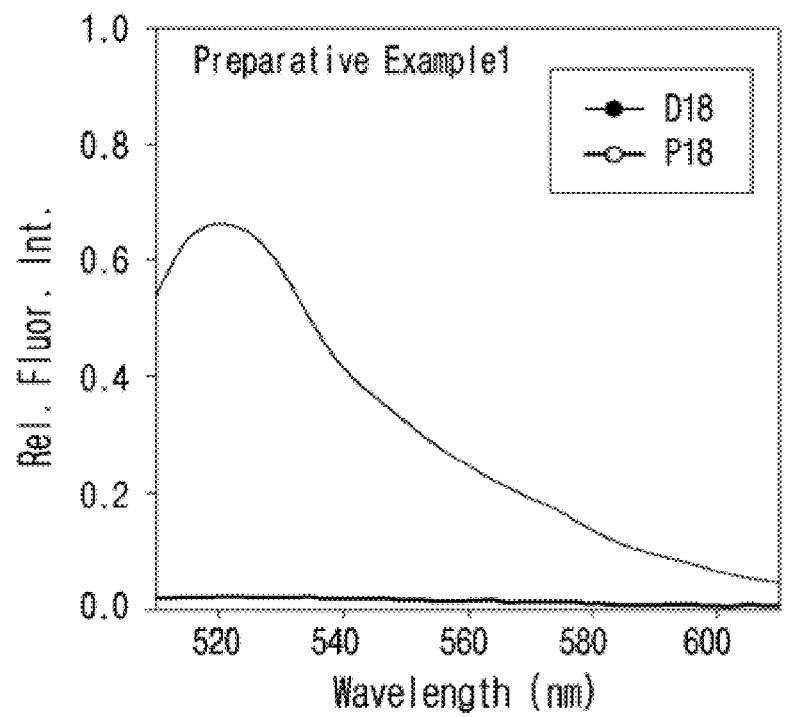
Figure 4F:
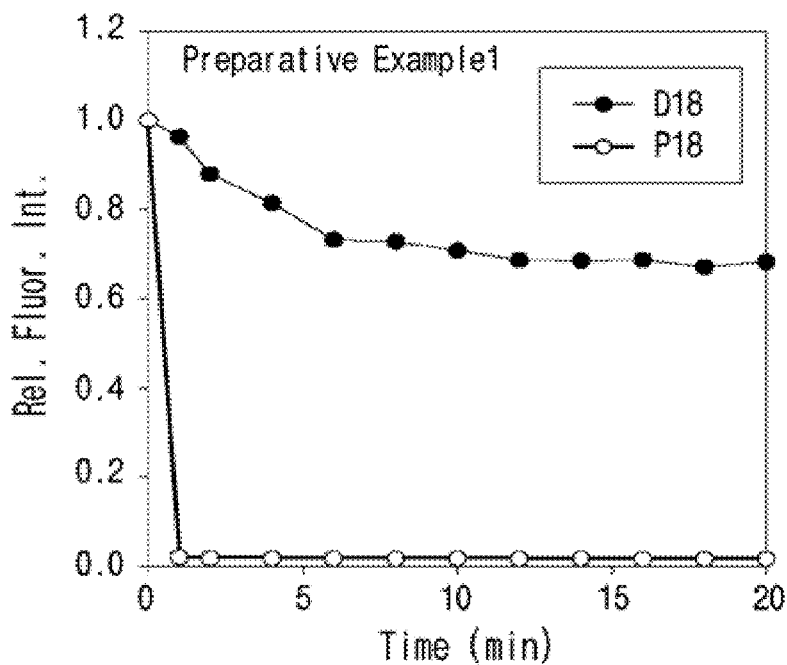

At the optimum amount of PEG-GO (4 μg/mL) for complete adsorption of PNA, confirmed in Experimental Example 2, the difference in relative fluorescence values of the PEG-GO of Preparative Example 1 between D18 and P18 was 66% of the initial value (FIG. 4B), while that of the GO—COOH of Comparative Example 1 was 32% (2 μg/mL; FIG. 4E). Moreover, the quenching phenomenon of D18 in the presence of the PEG-GO of Preparative Example 1 was stabilized in a shorter time than that in the presence of the GO—COOH of Comparative Example 1 (FIGS. 4C and 4F). These results suggested that the PEG modification selectively disrupted the approach of highly hydrophilic DNA onto the GO surface by providing a water barrier.

<Experimental Example 3> Confirmation of Inhibition of Dz Activity by PNA

In order to confirm the inhibition of Dz activity by PNA, the Dz/P18 duplex of Example 1 and the free Dz without PNA of Comparative Example 2 were prepared. Then, they were added to 1×Dz buffer containing hemin as a DNAzyme cofactor and 2,2'-azino-bis(3-ethylbenzothiazoline-6-sulfonic acid) (ABTS) and $H_2O_2$ as colorimetric reagents. And, as a negative control, only 1×Dz buffer containing hemin, 2,2'-azino-bis(3-ethylbenzothiazoline-6-sulfonic acid) (ABTS) and $H_2O_2$ was prepared. The results are shown in FIGS. 2A to 2D.

3-1. Observation of Color Change with Naked Eye

In 1×Dz buffer containing hemin, ABTS, and H2O2, the free Dz without PNA of Comparative Example 2 could produce green-colored ABTS by folding into a G-quadruplex structure with hemin. However, under the same conditions, the Dz/P18 duplex of Example 1 showed little color change, similar to the negative control (FIG. 2F). These results indicated that PNA hybridization with Dz inhibited the formation of the G-quadruplex structure of Dz and successfully switched off the Dz activity.

3-2. Measurement of Color Change by Colorimetric Method

Figure 2C:
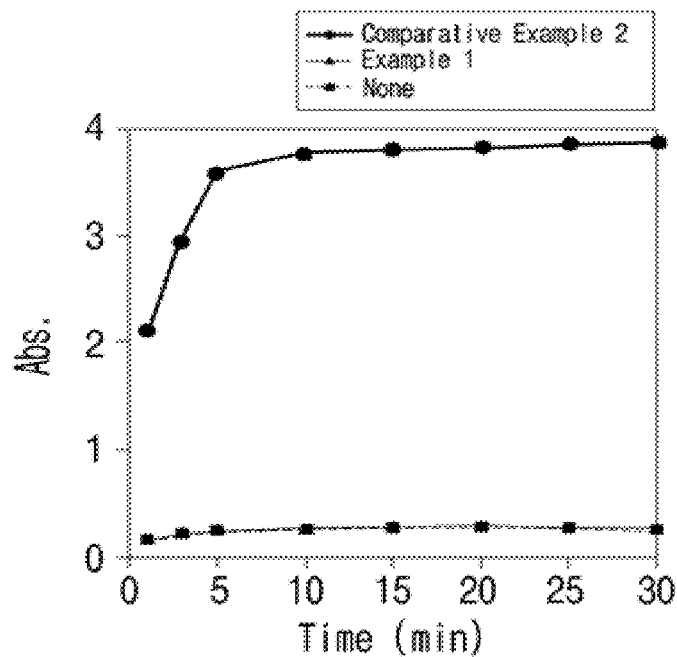
FIGS. 2C and 2D are diagrams showing the time-dependent absorbance at 420 nm and the absorbance spectra at 30 min in the presence of a Dz cofactor of Comparative Example 2, a color reagent of Example 1, and the negative control peroxide.
Figure 2D:
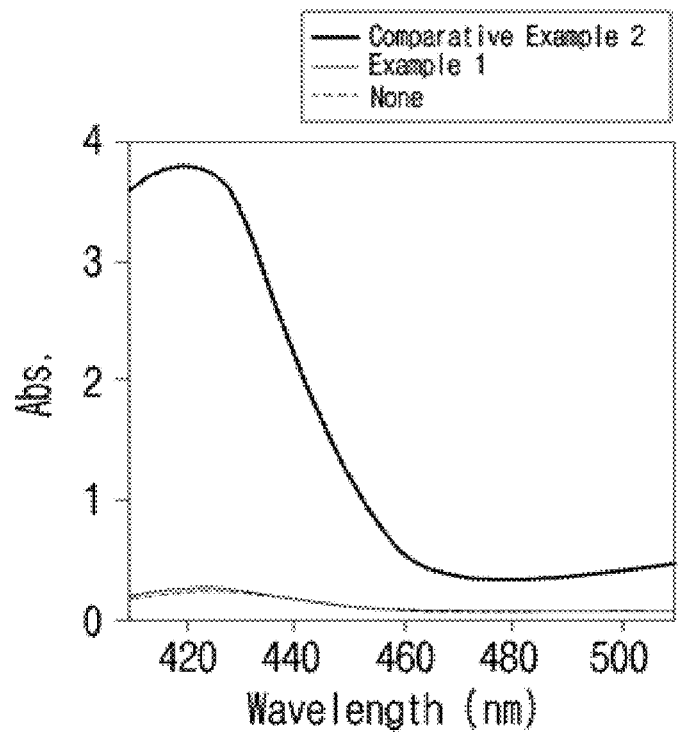

The distinct color difference between the Dz/P18 duplex of Example 1, the free Dz without PNA of Comparative Example 2, and the negative control was confirmed spectrophotometrically at A420 using a microplate reader. As a result, A420 values of the Dz/P18 duplex of Example 1 and the negative control were almost unchanged, whereas A420 of the free Dz without PNA of Comparative Example 2 was dramatically increased within a few minutes (FIGS. 2C and 2D). These results indicated that PNA hybridization with Dz inhibited the formation of the G-quadruplex structure of Dz and successfully switched off the Dz activity.

<Experimental Example 4> Confirmation of Colorimetry of Temperature Sensor According to Concentration of PEG-GO The Dz/P18 duplex of Example 2 and the Dz/P18 duplex of Comparative Example 3 were prepared to optimize the amount of PEG-GO to be used for the temperature sensor according to the present invention, and fluorescence intensity and absorbance were measured. The results are shown in FIGS. 5A to 5D.

4-1. Measurement of Color Change by Fluorescence Intensity

Figure 5A:
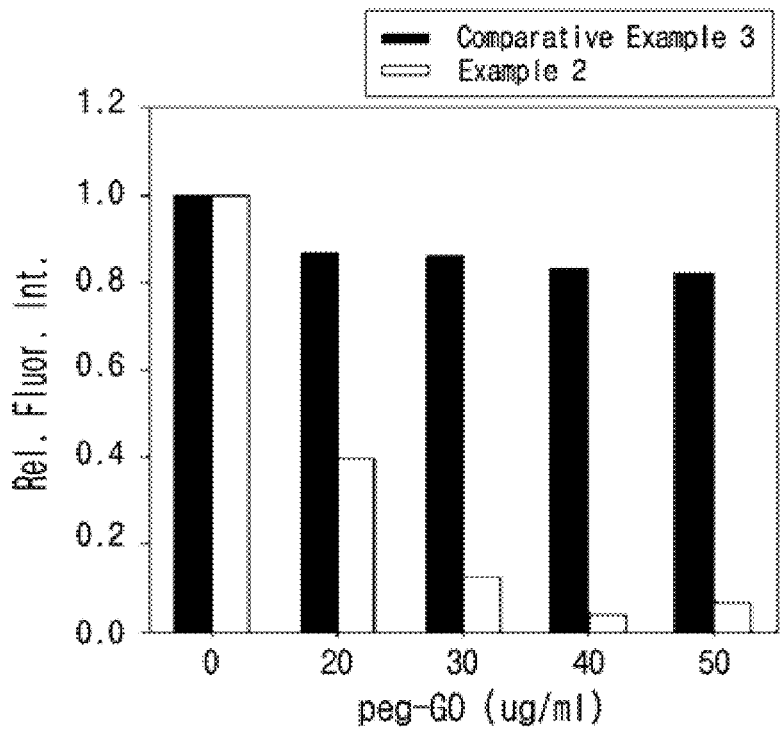
FIG. 5A, FIG. 5B, FIG. 5C, and FIG. 5D are set of graphs showing the fluorescence intensity and absorbance when the Dz/P18 duplex dissociated by heating (Example 2) or stored at room temperature without heating (Comparative Example 3) was mixed with various PEG-GOs.
Figure 5B:
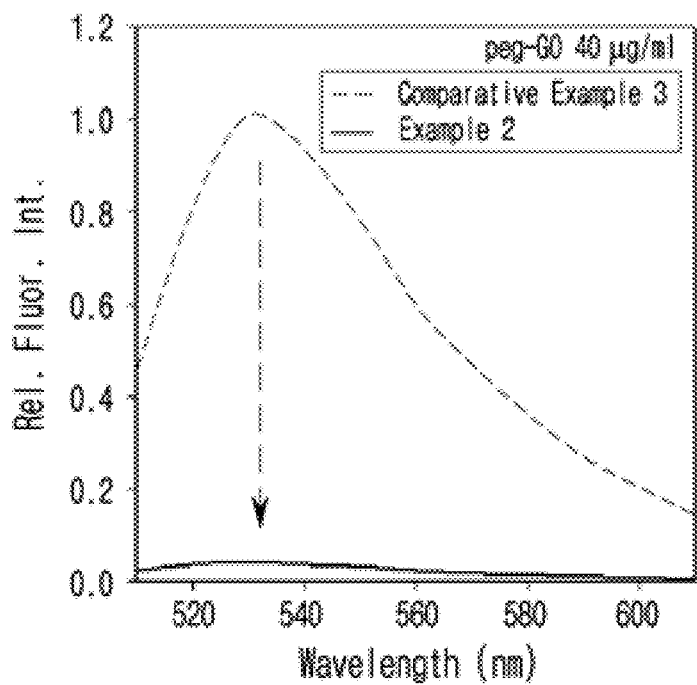

As shown in FIG. 5A, the relative fluorescence intensity of the heated Dz/P18 of Example 2 was decreased as the amount of PEG-GO increased, whereas the relative fluorescence intensity of the Dz/P18 of Comparative Example 3 without heating showed minor changes depending on the increase in concentration of PEG-GO. This difference in the quenching phenomenon indicated that PEG-GO could act as an effective scavenger for PNA by capturing the single-stranded P18 after denaturation of Dz/P18. When concentrations of more than 40 μg/mL PEG-GO were used, the heated Dz/P18 of Example 2 exhibited over 95% quenching efficiency (FIG. 5B).

4-2. Measurement of Color Change by Colorimetric Method

The present inventors performed an additional colorimetric assay by simply adding H2O2 in the same mixtures to verify the folding of Dz into the G-quadruplex structure, after PNA adsorption on PEG-GO.

Figure 5C:
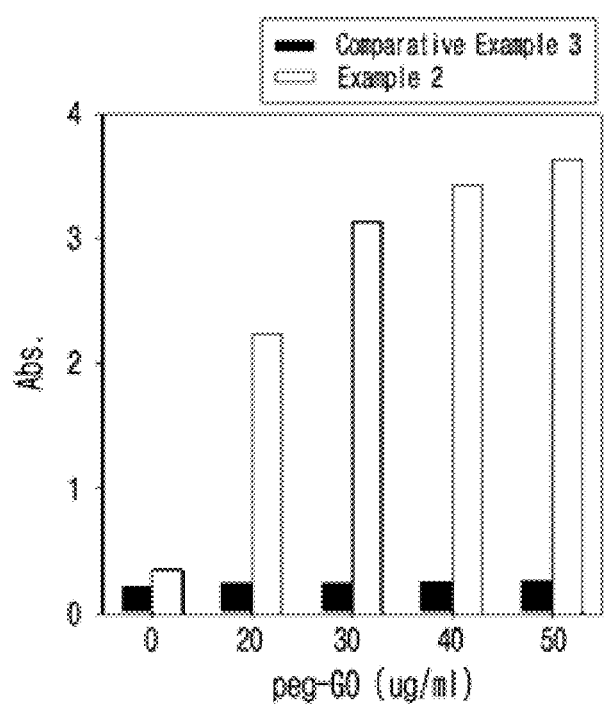
Figure 5D:
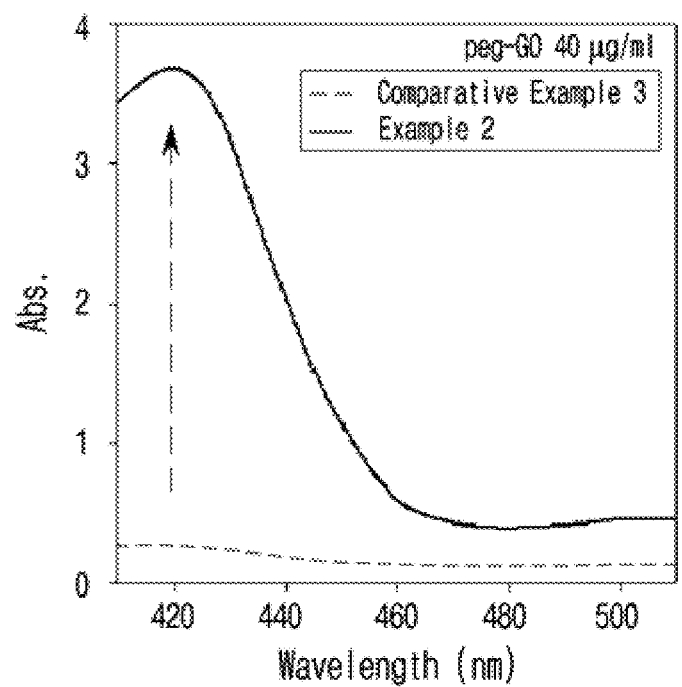

As shown in FIG. 5C, the A420 of the heated Dz/P18 of Example 2 increased as the concentration of PEG-GO increased, whereas the A420 of the Dz/P18 of Comparative Example 3 maintained minimum values below 0.3. Therefore, it was confirmed that PEG-GO selectively captured denatured P18 at high temperatures and prevented rehybridization between Dz and P18. The free Dz could fold into the G-quadruplex structure, allowing catalytic reactions in the presence of hemin to cause color change.

<Experimental Example 5> Confirmation of Colorimetry of Temperature Sensor According to Temperature For high-resolution temperature sensing with PEG-GO, the present inventors observed both colorimetric and fluorescence signals of Dz/P18 with PEG-GO in the presence of hemin and ABTS after applying temperatures ranging from 50° C. to 80° C. at intervals of 2° C. The results are shown in FIG. 6a to 6d.

Figure 6A:
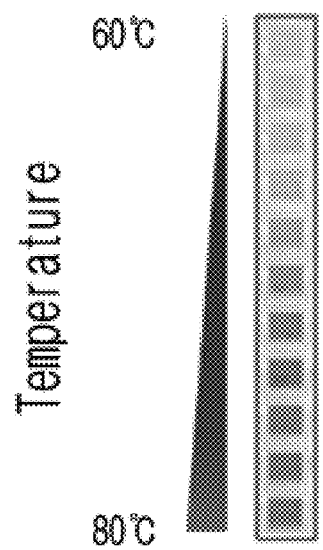
FIG. 6A, FIG. 6B, FIG. 6C, and FIG. 6D are set of graphs showing the results of measuring the fluorescence intensity and absorbance by heating the product of Example 2 in a temperature range from 5° C. to 80° C.

When PEG-GO and Dz/P18 in the buffer solution were heated to the target temperature and $H_2O_2$ was added, a color change into dark green was observed with the naked eye according to the increase in temperature (FIG. 6A). As the temperature increased, more Dz/P18 denaturation occurred, and as a result, as the free Dz regaining the catalytic activity increased, it bound to hemin to catalyze the oxidation reaction of ABTS.

Figure 6B:
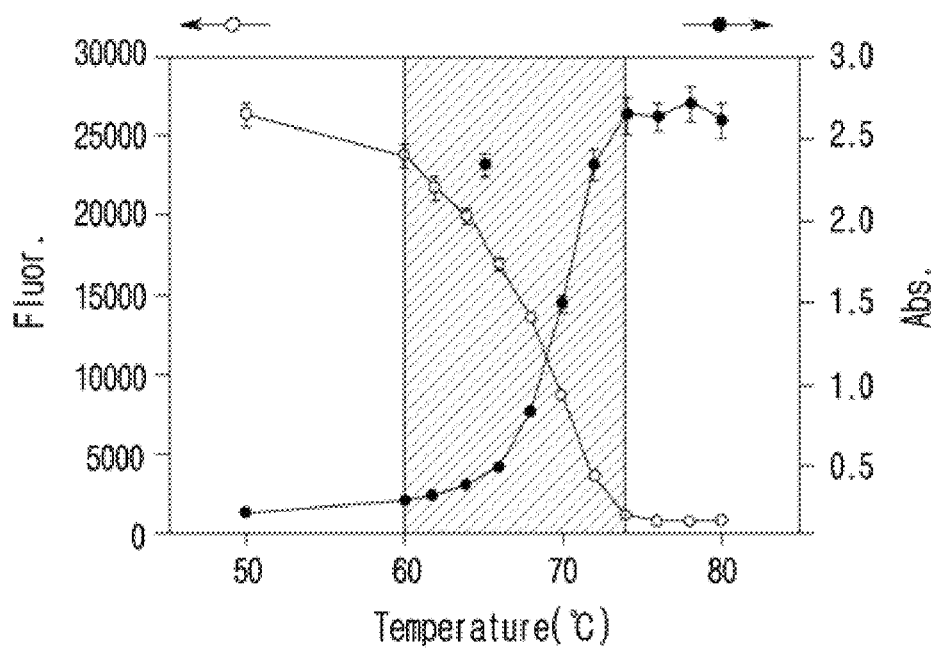
Figure 6C:
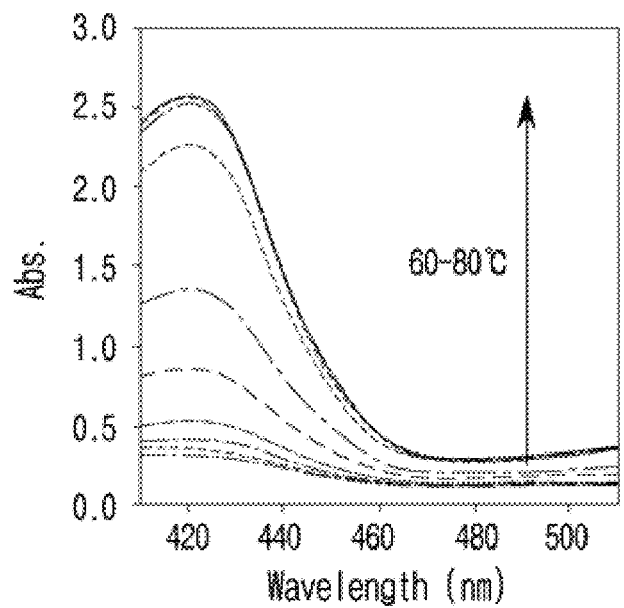
Figure 6D:
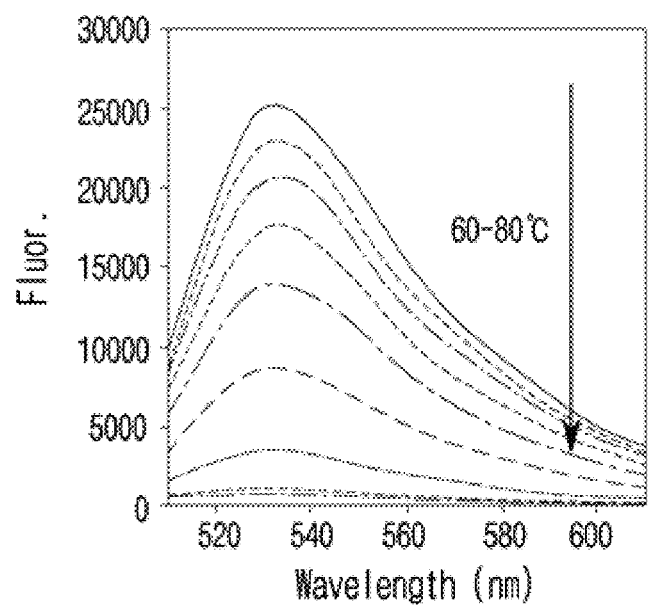

The change to darker color as the temperature increased was also quantitatively measured by measuring A420 and fluorescence intensity. The results are shown in FIGS. 6B and 6C.

As a result, the graph of absorbance showed a sigmoidal shape similar to the DNA melting curve. In this temperature range, the fluorescence intensity of the same solution decreased as the temperature increased, indicating that selective adsorption of P18 on PEG-GO was followed by temperature-dependent denaturation of Dz/P18. This opposite tendency of the fluorescence intensity and the absorbance observed in Experimental Example 5 indicated that Dz-catalyzed color development directly reflected the temperature-dependent denaturation of Dz/P18 and activation of free Dz. In particular, in the range from 60° C. to 74° C., there were a major difference in both the absorbance and fluorescence values as the temperature increased, allowing high-resolution sensing of temperature. Therefore, it was confirmed that the temperature could be discriminated by visible color change as well as quantitative measurement of absorbance.

<Experimental Example 6> Confirmation of Colorimetry of Temperature Sensor According to Number of Base Pairing-1

By changing the length of the PNA strand, the thermal stability of Dz/PNA can be controlled. Thus, the Dz/P18 duplex of Example 1, the Dz/P9 duplex of Example 3, and the Dz/P12 duplex of Example 4 were prepared, and then a temperature-dependent color development experiment across the broad temperature range of 20~80° C. was performed. The Dz/P18 duplex of Example 1, the Dz/P9 duplex of Example 3, or the Dz/P12 duplex of Example 4 were mixed with PEG-GO in 1×Dz buffer containing hemin and ABTS, and the mixture was incubated at intervals of 10° C. for 5 minutes. Once H2O2 was added to the mixture, the color change was observed. The results are shown in FIGS. 7A to 7E.

6-1. Observation of Color Change with Naked Eye

First, before temperature sensing, all of the Dz/P18 duplex of Example 1, the Dz/P9 duplex of Example 3, and the Dz/P12 duplex of Example 4 showed colorless at 4° C. Through this, it was confirmed that the Dz activity was inhibited by PNA (FIG. 7A). Once H2O2 was added to the mixture, a green color was gradually observed as the temperature increased (FIG. 7B). The Dz/P18 duplex of Example 1, the Dz/P9 duplex of Example 3, and the Dz/P12 duplex of Example 4 displayed visible color changes at 20° C., 40° C., and 60° C., respectively.

6-2. Measurement of Color Change by Colorimetric Method

For the Dz/P18 duplex of Example 1, the relative A420 showed a dramatic increase in the range of 60~80° C. (FIG. 7C), which coincided with the data shown in FIG. 6b. Shortening the length of the PNA probe caused the absorbance curve to shift to the left along the temperature axis. From the above results, it was confirmed that the shorter the length of the PNA probe, the lower the temperature at which denaturation occurred, and the color change appeared at the lower temperature.

6-3. Measurement of Color Change by Fluorescence Intensity

Figure 7D:
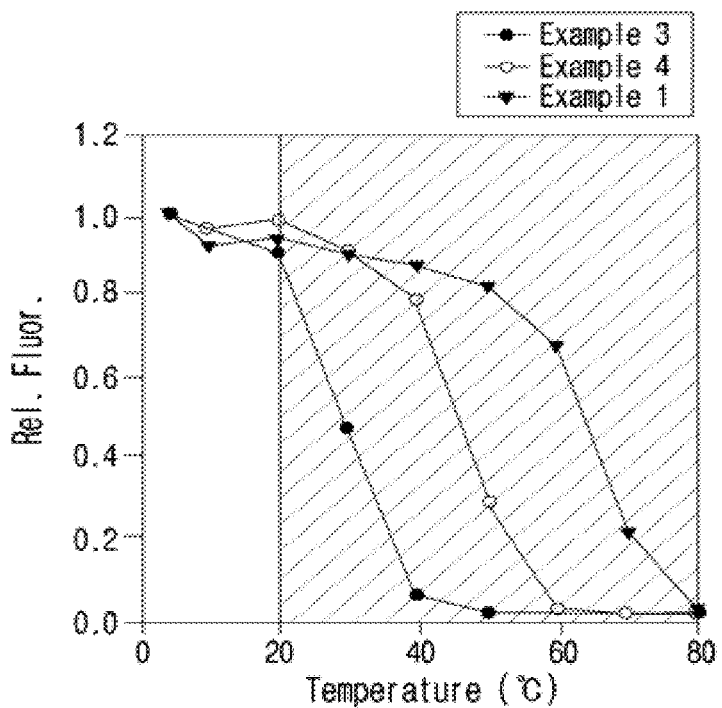

Fluorescence curves for the three Dz/PNA constructs of Example 1, Example 3 and Example 4 showed a reverse trend with each corresponding absorbance in the same temperature range (FIG. 7D). This indicated that the PNA length-dependent absorbance curve shift was dependent on the thermal stability of each Dz/PNA pair.

Figure 7E:
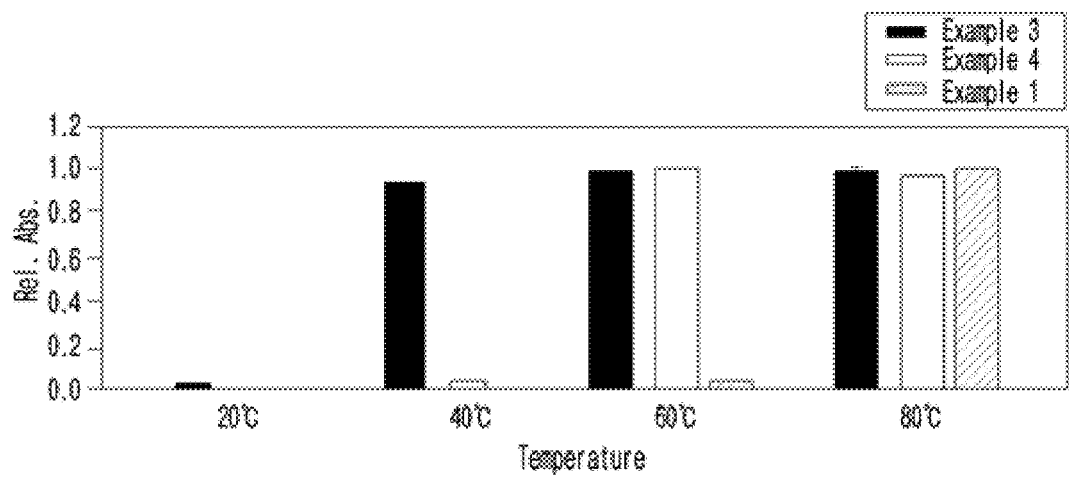

From the above experiments, the present inventors established the detectable temperature range by adjusting the thermal stability of Dz/PNA. As shown in FIG. 7e, the temperature-dependent color change could be evaluated as a bar-code (on/off) system by using a combination of PNA probes of varying lengths.

<Experimental Example 7> Confirmation of Temperature Recall Function

The present inventors demonstrated the temperature recall function by delaying the visualization of sensing results after the temperature sensor was applied at the target temperature.

Figure 8:
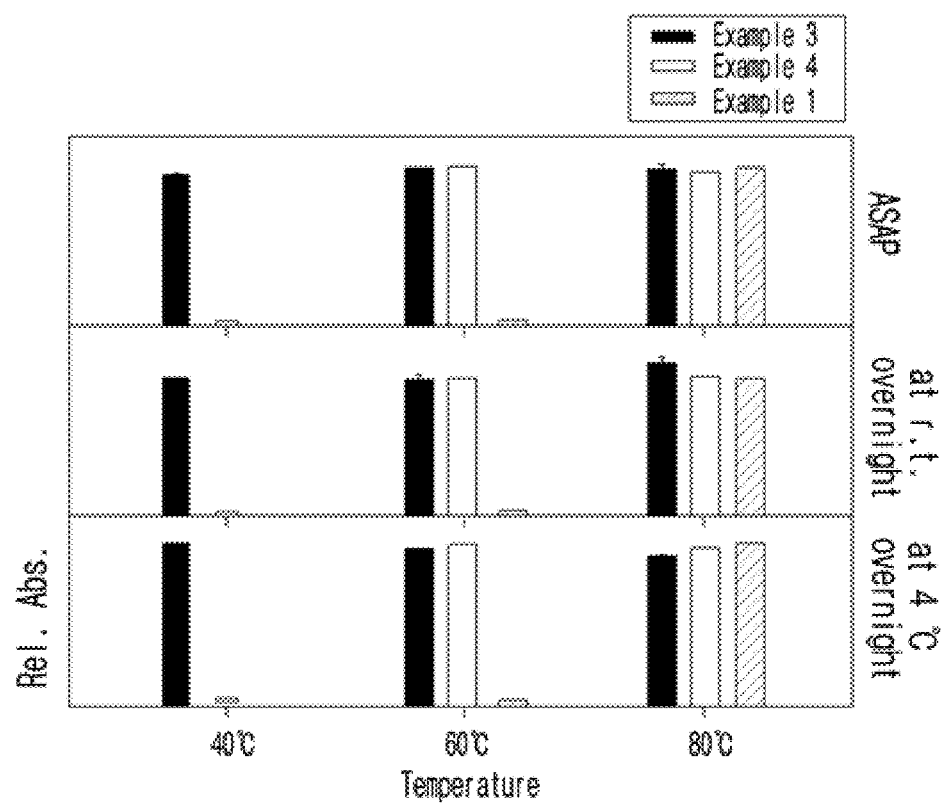
FIG. 8 is a set of graphs showing the relative absorbance values of the products of Examples maintained at the target temperatures, 40° C., 60° C. and 80° C., for 5 minutes and stored at room temperature or 4° C. overnight. $H_2O_2$ was added after storage or added immediately without storage.

Most DNA temperature sensors generally restrict measurements to the temperature at the time of analysis because the melting kinetics of DNA is reversible depending on temperature. However, since the temperature sensor according to the present invention has a temperature recall function, an experiment was conducted to confirm this. The present inventors chose three target points, i.e., 40° C., 60° C., and 80° C., to record the temperature using a sensor. Each mixture containing the Dz/PNA constructs of Example 1, Example 3 and Example 4, PEG-GO, hemin, and ABTS was maintained at the target temperature for 5 minutes and stored at room temperature or 4° C. overnight. Compared with the control group adding H2O2 immediately, both overnight-stored groups exhibited the same green color once H2O2 was added, regardless of the storage conditions (FIG. 8).

Because the adsorption of PNA on PEG-GO followed by Dz activation was irreversible, the ratio of active Dz at the target temperature could be recorded in the system according to the present invention. These results suggested that the temperature sensing system according to the present invention could memorize the target temperature, which could be analyzed with a recognizable barcode following addition of H2O2 at a later measurement time point.

Irreversible PNA capture on PEG-GO at the target temperature enabled recall of the temperature, which could permit delayed color development in the time of need, unlike typical DNA thermosensors. The visual thermosensor according to the present invention was technically convenient and can be easily applied and used. Moreover, the system according to the present invention was versatile and could be broadly applied to sensing a diverse range of temperatures by redesigning the PNA probes based on the melting temperature of Dz/PNA. The combined use of different PNA probes provided a bar-code result for more precise sensing of temperature.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

<Experimental Example 8> Confirmation of Colorimetry of Temperature Sensor According to Number of Base Pairing-2

Figures 9A, 9B:
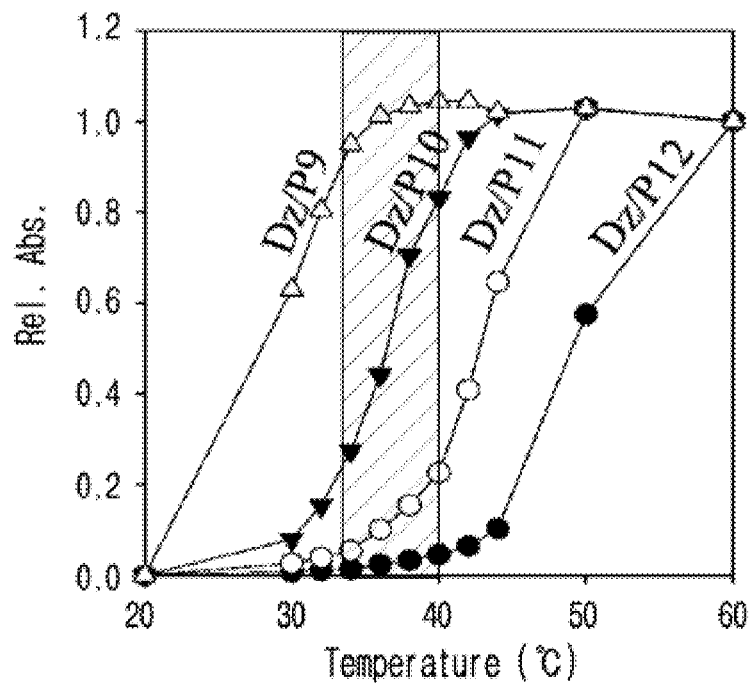
FIG. 9A, FIG. 9B, FIG. 9C, and FIG. 9D are a set of diagrams showing the results of measuring the fluorescence intensity and absorbance of the products of Example 3~Example 6 for colorimetric confirmation of the temperature sensor according to the number of base pairs. The sequences shown in FIG. 9A include Dz (SEQ ID NO: 1), P12 (SEQ ID NO: 3), P11 (SEQ ID NO: 9), P10 (SEQ ID NO: 10), and P9 (SEQ ID NO: 2).

To investigate the feasibility of this system in real-world applications, we tried to repeat the temperature measuring experiment at intervals of 2° C. in the body temperature range. We utilized a set of four PNA probes from 9 to 12 bases, i.e., P9, P10, P11, and P12, to enhance the detection accuracy around the target temperature (FIG. 9A). By changing the length of the PNA strand, the thermal stability of Dz/PNA can be controlled. Thus, the Dz/P12 duplex of Example 4, the Dz/P11 duplex of Example 6, Dz/P10 duplex of Example 5 and the Dz/P19 duplex of Example 3 were prepared, and then a temperature-dependent color development experiment across the broad temperature range of 20~60° C. was performed. The results are shown in FIG. 9a to 9d.

8-1. Measurement of Color Change by Colorimetric Method

For Dz/P10 and Dz/P11, the relative A420 showed a dramatic increase in the respective range of 30° C.-40° C. and 40° C.-50° C., which were positioned between established curves of Dz/P9 and Dz/P12 (FIG. 9B). Across the target range of 34° C.-40° C., Dz/P10 and Dz/P11 showed a gradual increase in A420 values, while Dz/P9 and Dz/P12 acted as maximized and minimized standards, respectively.

8-2. Observation of Color Change with Naked Eye and Smartphone Application

Figure 9C:
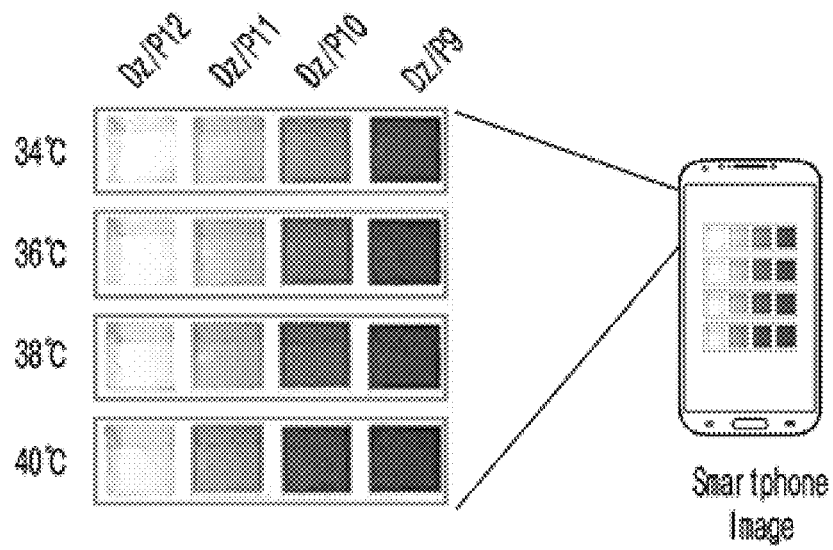
Figure 9D:
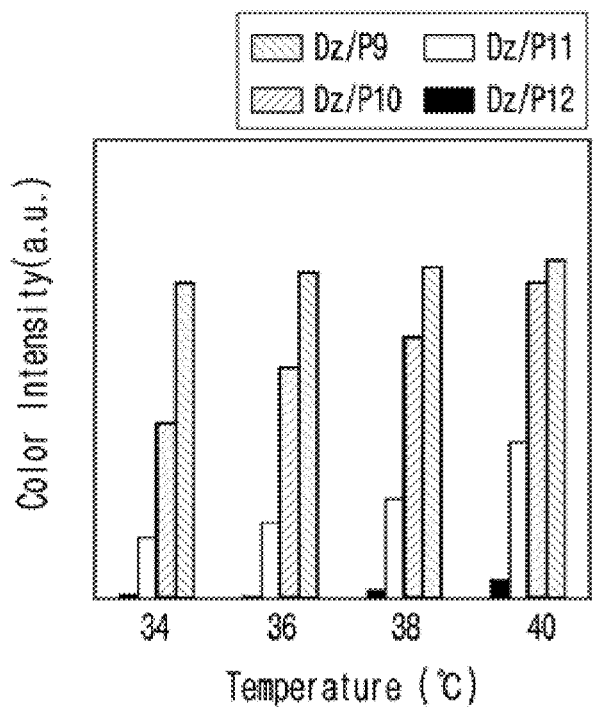

Each fine color change, hardly distinguishable by the naked eye, could be qualified by means of smartphone application. (FIGS. 9C and 9D). Moreover, the integrated intensities pattern of four Dz/PNAs provided more precise temperature information than a single Dz/PNA. These data demonstrated that the temperature resolution of this system could be enhanced by combining PNA probes with proper lengths and by using a smartphone.

What is claimed is:

1. A composition for sensing temperature comprising graphene oxide, a duplex comprising a DNAzyme strand complementarily linked to a PNA strand, and a DNAzyme cofactor, wherein the length of the duplex in which the DNAzyme strand and the PNA strand are complementarily linked is 9 to 18 nucleotides.

2. The composition for sensing temperature according to claim 1, wherein the duplex is denatured into a single strand at a certain temperature, and the DNAzyme strand binds to the DNAzyme cofactor.

3. The composition for sensing temperature according to claim 2, wherein the duplex is irreversibly denatured at a certain temperature.

4. The composition for sensing temperature according to claim 1, wherein the DNAzyme includes a G-quadruplex structure.

5. The composition for sensing temperature according to claim 1, wherein the graphene oxide is functionalized with polyethylene glycol (PEG-GO).

6. The composition for sensing temperature according to claim 1, wherein the composition further includes a colorimetric reagent.

7. The composition for sensing temperature according to claim 6, wherein the colorimetric reagent includes one or more reagents selected from the group consisting of ABTS (2,2'-T-azino-bis(3-ethylbenzothiazoline-6-sulfonic acid)), OPD (o-phenylenediamine dihydrochloride), DAB (di-aminobenzidine), AEC (3-amino-9-ethylcarbazole), TMB (3,3',5,5'-tetra Methylbenzidine), AmplexRed, and Homovanilic acid; and one or more peroxides.

8. The composition for sensing temperature according to claim 1, wherein the DNAzyme cofactor is hemin.

9. The composition for sensing temperature according to claim 1, wherein the composition for sensing temperature adjusts to the target temperature by adjusting the length of the PNA strand.

10. A method for temperature sensing comprising the following steps:
obtaining a mixture comprising the composition of claim 1,
and observing a color change of the mixture while heating the mixture.

11. The method according to claim 10, wherein the graphene oxide is functionalized with polyethylene glycol (PEG-GO).

12. The method according to claim 10, wherein the target temperature is adjusted to by adjusting the length of the PNA strand.

13. A kit for sensing temperature comprising the composition of claim 1.

14. The kit for sensing temperature according to claim 13, wherein the kit further includes a colorimetric reagent.

15. The kit for sensing temperature according to claim 13, wherein the graphene oxide is functionalized with polyethylene glycol (PEG-GO).

16. The kit for sensing temperature according to claim 13, wherein the target temperature is adjusted to by adjusting the length of the PNA strand.

* * * * *

SEQUENCE LISTING

<160> NUMBER OF SEQ ID NOS: 10

<210> SEQ ID NO 1
<211> LENGTH: 18
<212> TYPE: DNA
<213> ORGANISM: Artificial Sequence
<220> FEATURE:
<223> OTHER INFORMATION: DNAzyme

<400> SEQUENCE: 1
gggtagggcg ggttggga                                                    18

<210> SEQ ID NO 2
<211> LENGTH: 9
<212> TYPE: DNA
<213> ORGANISM: Artificial Sequence
<220> FEATURE:
<223> OTHER INFORMATION: PNA (P9)

<400> SEQUENCE: 2 acccgccct                                                               9

<210> SEQ ID NO 3
<211> LENGTH: 12
<212> TYPE: DNA
<213> ORGANISM: Artificial Sequence
<220> FEATURE:
<223> OTHER INFORMATION: PNA (P12)

<400> SEQUENCE: 3
caacccgccc ta                                                          12

<210> SEQ ID NO 4
<211> LENGTH: 18
<212> TYPE: DNA
<213> ORGANISM: Artificial Sequence
<220> FEATURE:
<223> OTHER INFORMATION: PNA (P18)

<400> SEQUENCE: 4
tcccaacccg ccctaccc                                                    18

<210> SEQ ID NO 5
<211> LENGTH: 24
<212> TYPE: DNA
<213> ORGANISM: Artificial Sequence
<220> FEATURE:
<223> OTHER INFORMATION: DNAzyme

<400> SEQUENCE: 5
gtggggcatt gtgggtgggt gtgg                                             24

<210> SEQ ID NO 6
<211> LENGTH: 18
<212> TYPE: DNA
<213> ORGANISM: Artificial Sequence
<220> FEATURE:
<223> OTHER INFORMATION: DNAzyme

<400> SEQUENCE: 6
gtgggtaggg cgggttgg                                                    18

<210> SEQ ID NO 7
<211> LENGTH: 26
<212> TYPE: DNA
<213> ORGANISM: Artificial Sequence
<220> FEATURE:
<223> OTHER INFORMATION: DNAzyme

<400> SEQUENCE: 7
ggtggtggtg gttgtggtgg tggtgg                                           26

<210> SEQ ID NO 8
<211> LENGTH: 21
<212> TYPE: DNA

```
<213> ORGANISM: Artificial Sequence
<220> FEATURE:
<223> OTHER INFORMATION: DNAzyme

<400> SEQUENCE: 8
gggttagggt tagggttagg g                                             21

<210> SEQ ID NO 9
<211> LENGTH: 11
<212> TYPE: DNA
<213> ORGANISM: Artificial Sequence
<220> FEATURE:
<223> OTHER INFORMATION: PNA (P11)

<400> SEQUENCE: 9
aacccgccct a                                                        11

<210> SEQ ID NO 10
<211> LENGTH: 10
<212> TYPE: DNA
<213> ORGANISM: Artificial Sequence
<220> FEATURE:
<223> OTHER INFORMATION: PNA (P10)

<400> SEQUENCE: 10
acccgcccta                                                          10
```